United States Patent

Hou et al.

Patent Number: 5,461,147
Date of Patent: Oct. 24, 1995

[54] PROCESS FOR PREPARING BENZAZEPINE INTERMEDIATES FOR THE SYNTHESIS OF D1 ANTAGONISTS

[75] Inventors: Donald Hou, Verona; Richard W. Draper, North Caldwell; Gary M. Lee, Murray Hill; Janet L. Mas, Scotch Plains, all of N.J.

[73] Assignee: Schering Corporation, Kenilworth, N.J.

[21] Appl. No.: 127,667

[22] Filed: Sep. 27, 1993

[51] Int. Cl.[6] .................. C07C 217/70; C07C 271/16; C07D 223/14
[52] U.S. Cl. .............. 540/576; 560/27; 560/28; 560/29; 564/355; 564/308; 548/228
[58] Field of Search ............ 540/576; 564/355; 560/27

[56] References Cited

U.S. PATENT DOCUMENTS

| | | | |
|---|---|---|---|
| 2,160,138 | 5/1939 | Gaylor | 564/355 |
| 4,973,586 | 11/1990 | Berger et al. | 514/217 |

OTHER PUBLICATIONS

Berger, et al, *J. Med. Chem.*, 32, 1913–1921 (1989).

*Primary Examiner*—Philip I. Datlow
*Attorney, Agent, or Firm*—Paul A. Thompson

[57] ABSTRACT

Disclosed are a process and intermediates of the formula

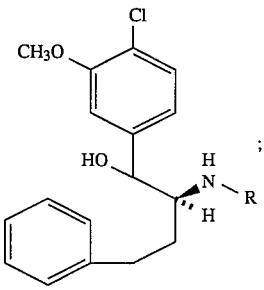

wherein R is —$CH_3$ or —C(O)—$OR^1$, and $R^1$ is $C_1$-$C_6$ alkyl or —$CH_2C_6H_5$; or the formula

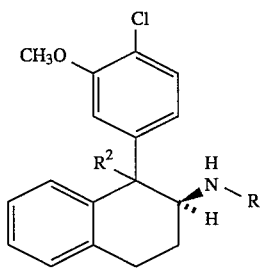

wherein: $R^2$ is H or OH, R is —C(O)$OR^1$ and $R^1$ is $C_1$-$C_6$ alkyl or —$CH_2C_6H_5$, or where $R^2$ is H, R can also be $CH_3$; for preparing benzazepine intermediates of the formula

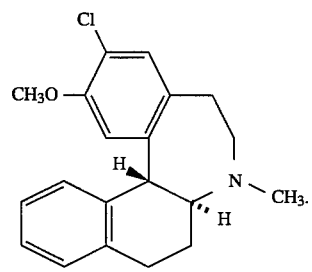

The benzazepine intermediates are useful for preparing benzazepines having activity as selective D1 receptor antagonists.

8 Claims, No Drawings

PROCESS FOR PREPARING BENZAZEPINE INTERMEDIATES FOR THE SYNTHESIS OF D1 ANTAGONISTS

BACKGROUND OF THE INVENTION

The present invention relates to a process for preparing intermediates useful in the preparation of benzazepines having activity as selective D1 receptor antagonists.

U.S. Pat. No. 4,973,586 discloses fused benzazepines, and in particular the compound known as SCH 39166, having the structure

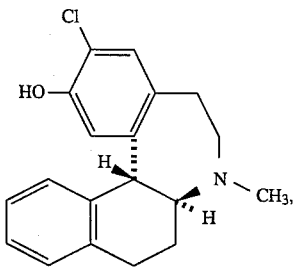

as selective D1 antagonists useful in the treatment of psychoses, depression, pain and D1 dependent neurological disorders. Methods for preparing such compounds are also described therein.

Berger, et al, *J. Med. Chem.*, 32, 1913–1921 (1989), discloses a process for preparing SCH 39166 comprising acid promoted cyclization of a compound of the formula (1) to give a 1:1 mixture of cis and trans benzazepines (cis-2 and trans-2, respectively). Compound trans-2 is then converted to racemic compound I via a multi-step procedure. Compound I is resolved via its di-O,O'-p-tolyltartrate salt and hydrolyzed with HBr and HOAc to give SCH 39166. process or that the chiral centers be introduced using inexpensive chiral

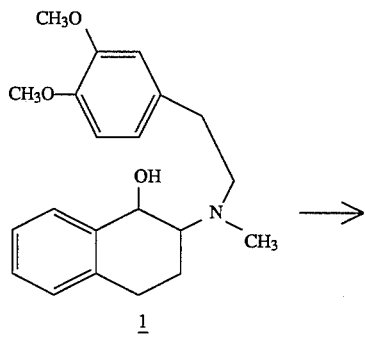

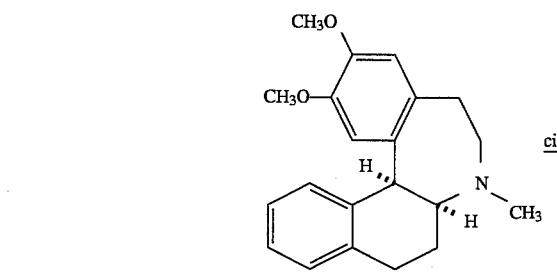

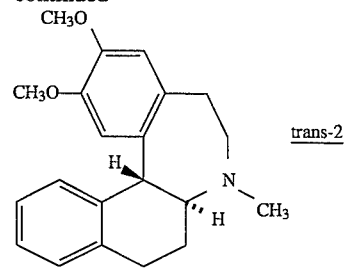

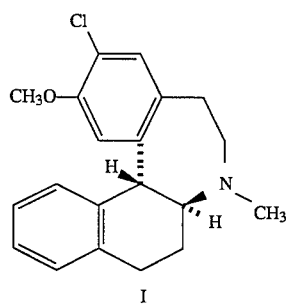

The prior art process suffers from several shortcomings. It is inefficient, producing a 1:1 mixture of cis and trans benzazepines in the cyclization step. In addition, conducting the resolution step at a late stage of the synthesis is very costly and adds further inefficiency. Therefore, it was desirable to develop a chemically efficient and cost effective process for preparing SCH 39166 of high optical purity. It was also desired that the resolution be performed at an early stage of the process or that the chiral centers be introduced using inexpensive chiral starting materials, thereby avoiding the need for resolution.

SUMMARY OF THE INVENTION

The present invention comprises a process for preparing compounds of the formula I

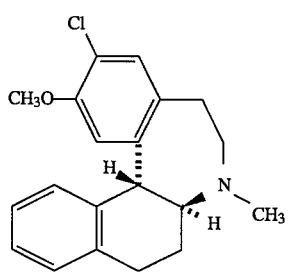

comprising the steps:

(a) cyclizing an alcohol of the formula

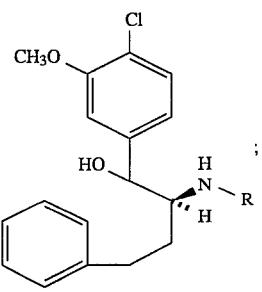

wherein R is —CH₃ or —C(O)—OR¹, and R¹ is $C_1$-$C_6$ alkyl or —CH₂C₆H₅; and, where R is —C(O)—OR¹, reducing the cyclyzed product with a hydride reducing agent; to form an amine of the formula

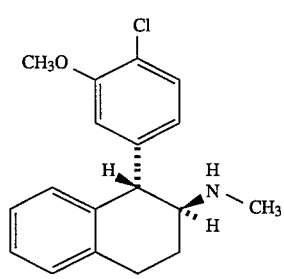

(b) reacting the amine of Step (a) with a compound of the formula J—CH₂—Q, wherein J is a leaving group and Q is a group of the formula

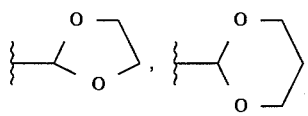

wherein $R^2$ is $C_1$-$C_6$ alkyl, to form a compound of the formula

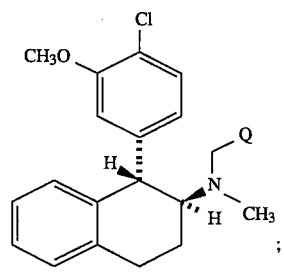

(c) cyclizing the product of step (b) and treating the cyclized product with a hydride reducing agent to give a compound of formula I.

The present invention further comprises a process, designated Process A, for preparing compounds of the formula I, wherein the alcohol of step (a) is prepared by a process comprising the steps:

(A1) treating L-homophenylalanine with an $C_1$-$C_6$ alkyl or benzyl chloroformate in the presence of a strong base to form a carbamate of the formula

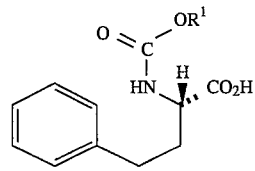

wherein $R^1$ is as defined above;

(A2) treating the carbamate of step (A1) with paraformaldehyde in the presence of an acid catalyst to form an oxazolidinone of the formula

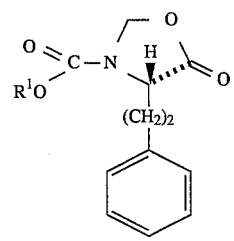

wherein $R^1$ is as defined above;

(A3) treating the oxazolidinone of step (A2) with a reagent of the formula

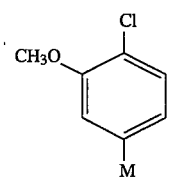

wherein M is selected from MgL, ZnL, TiL₃, CeL₂, MnL or CuL, and L is a halide selected from Br, Cl or I, to form a 5-hydroxy-oxazolidine of the formula

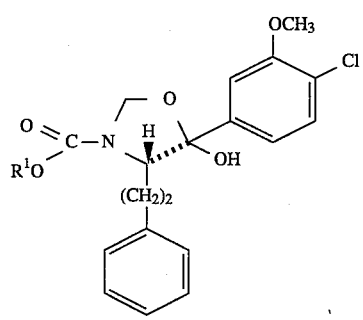

(A4) converting the 5-hydroxyoxazolidine of step (A3) to an alcohol of Step (a) by:

(i) treating the 5-hydroxyoxazolidine with an acid selected from BF₃.OEt₂, HCl, pTSA and HClO₄ to form a ketone of the formula

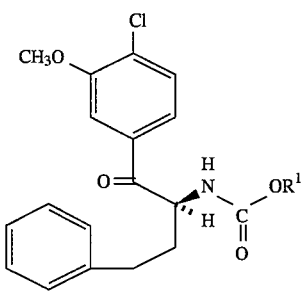

wherein R¹ is as defined above and treating the ketone of step (A4) with a hydride reducing agent; or (ii) treating the 5-hydroxyoxazolidine with a hydride reducing agent; to form the alcohol of Step (a).

In an alternative embodiment, the present invention further comprises a process, designated Process B, for preparing compounds of the formula I wherein the alcohol of step (a) is prepared by a process comprising the steps:

(B 1) treating the carbamate of step (A1) of Process A:

(i) with CH₃O—N(H)CH₃ or CH₃)—N(H)CH₃.HCl in the presence of BOP and a tertiary amine base; or (ii) with SOCl₂ or (COCl)₂ to form an acid chloride and treating the acid chloride with CH₃O—N(H)CH₃ or CH₃O—N(H)CH₃.HCl and pyridine; to give a compound of the formula

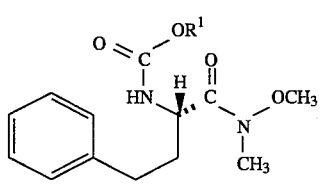

wherein R¹ is as defined above;

(B2) treating the product of step (B1) with a reagent of the formula

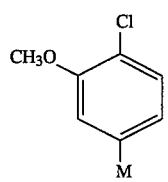

wherein M is selected from MgL, ZnL, TiL₃, CeL₂, MnL or CuL, and L is a halide selected from Br, Cl or I, to form a ketone of the formula

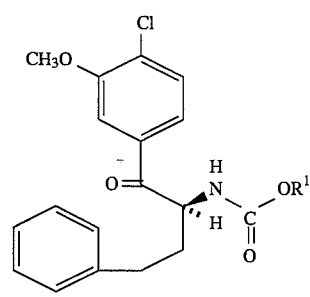

wherein R¹ is as defined above;

(B3) treating the ketone of step (B2) with a hydride reducing agent to form the alcohol of Step (a).

In a second alternative embodiment, the present invention comprises a process, designated Process C, for preparing a compound of the formula I comprising the steps:

(C1) reacting a ketocarbamate of the formula

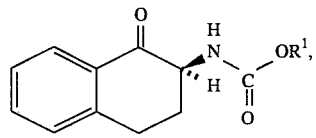

wherein R¹ is as defined above, with the lithium reagent prepared from 5-bromo-2-chloroanisole and t-butyllithium, to form a compound of the formula

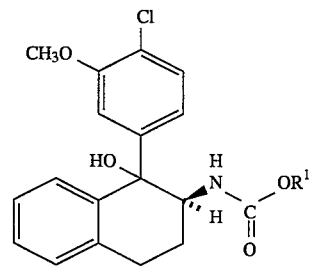

wherein R¹ is as defined above;

(C2) reacting the product of step (C1) with a trialkylsilane and CF₃CO₂H to form a compound of the formula

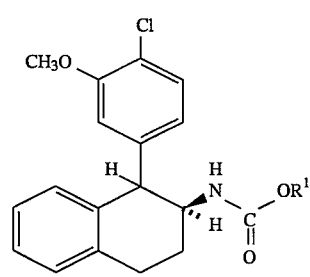

wherein R¹ is as defined above, as a mixture of cis and trans isomers;

(C3) reducing the product of step (C2) by treating with a hydride reducing agent to form a compound of the formula

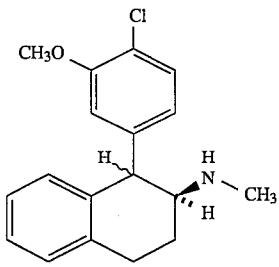

as a mixture of cis and trans isomers;

(C4) reacting the product of Step (C3) with a compound of the formula J—CH$_2$—Q, wherein J is a leaving group and Q is a group of the formula

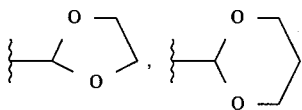

wherein R$^2$ is C$_1$-C$_6$ alkyl, to form a compound of the formula

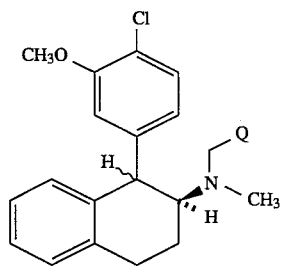

as a mixture of cis and trans isomers;

(C5) treating the product of step (C4) with an alkoxide base to form a compound of the formula

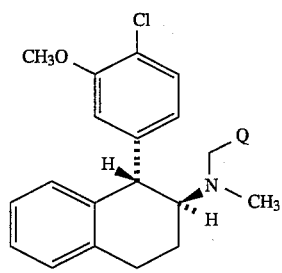

(C6) cyclizing the product of step (C5) to form the compound of formula I.

Preferred is a process of the present invention wherein: the cyclization of Step (a) comprises treating the alcohol with a strong acid, preferably CH$_3$SO$_3$H; the hydride reducing agent of step (a) is LiAlH$_4$; J is Br; Q is —CH(OR$^2$)$_2$ and R$^2$ is CH$_3$; and the cyclization of Step (c) comprises treating with a strong acid, preferably H$_2$SO$_4$ or CH$_3$SO$_3$H, followed by treatment with a hydride reducing agent, preferably TBAB or NaBH$_4$.

Also preferred is a process according to Process A, wherein: R$^1$ is CH$_3$— or CH$_3$CH$_2$—; the alkyl chloroformate of Step (A1) is methyl or ethyl chloroformate; the strong base of step (A1) is NaOH, preferably 1N NaOH; the acid catalyst of Step (A2) is p-TSA; the metal of Step (A3) is MgBr; and the hydride reducing agents of Steps (A4) (i) and (A4) (ii) are LiBH$_4$, LiAlH$_4$ or NaBH$_4$.

Another preferred process is the process according to Process B, wherein: R$^1$ is CH$_3$— or CH$_3$CH$_2$—; the tertiary amine base of Step (B1) is Et$_3$N or pyridine; M is Li, Na or MgBr; and the hydride reducing agent of Step (B3) is LiBH$_4$, LiAlH$_4$ or NaBH$_4$.

Yet another preferred process is the process according to Process C, wherein: R$^1$ is CH$_3$— or CH$_3$CH$_2$—; the trialkylsilane of Step (C2) is triethylsilane; the hydride reducing agent of Step (C3) is LiAlH$_4$; J is Br; the alkoxide base of Step (C5) is KOC(CH$_3$)$_3$ or NaOC(CH$_3$)$_3$; and the cyclization of Step (C6) comprises treating with a strong acid, preferably H$_2$SO$_4$ or CH$_3$SO$_3$H, followed by treatment with a hydride reducing agent, preferably TBAB or NaBH$_4$.

The process of the present invention does not suffer the shortcomings of the prior art process. It is chemically efficient and, by utilizing inexpensive chiral starting materials produces a chiral product (compound I) which is readily converted to SCH 39166 by known methods.

The present invention further comprises compounds of the formula

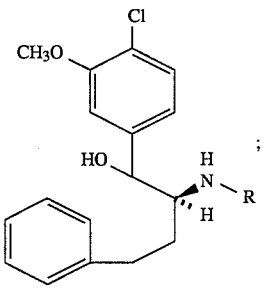

wherein R is —CH$_3$ or —C(O)—OR$^1$, and R$^1$ is C$_1$-C$_6$ alkyl or —CH$_2$C$_6$H$_5$, useful as intermediates in the preparation of benzazepines having activity as selective D1 receptor antagonists.

In another embodiment, the present invention further comprises compounds of the formula

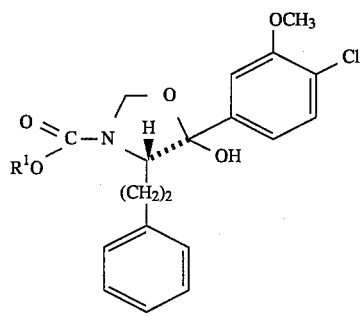

wherein R$^1$ is C$_1$-C$_6$ alkyl or —CH$_2$C$_6$H$_5$, useful as intermediates in the preparation of benzazepines having activity as selective D1 receptor antagonists.

In yet another embodiment, the present invention further comprises compounds of the formula

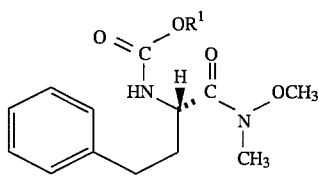

wherein $R^1$ is $C_1$-$C_6$ alkyl or —$CH_2C_6H_5$, useful as intermediates in the preparation of benzazepines having activity as selective D1 receptor antagonists.

In still another embodiment, the present invention further comprises compounds of the formula

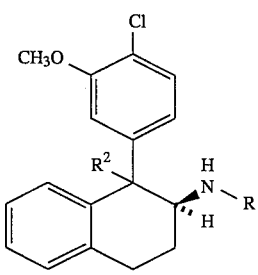

wherein: $R^2$ is H or OH, R is —$C(O)OR^1$, and $R^1$ is $C_1$-$C_6$ alkyl or —$CH_2C_6H_5$, or where $R^2$ is H, R can also be $CH_3$, useful as intermediates in the preparation of benzazepines having activity as selective D1 receptor antagonists.

DETAILED DESCRIPTION

In general, stereochemical representations are meant to denote absolute stereochemistry. The process of the present invention utilizes optically active starting materials and produces a single enantiomer of compound I. The stereochemical purity of compounds is generally given in terms of the enantiomeric excess (e.e.).

As used herein the term "alkyl" means a straight or branched alkyl chains of 1 to 6 carbon atoms;

"hydride reducing agent" means $LiAlH_4$, $NaBH_4$, $NaBH_3CN$, $LiBH_4$ or a borane amine complex, such as borane-methylamine, borane-tert-butylamine, borane-piperidine, borane-triethylamine, borane-N,N-diisopropylethylamine, borane-N,N-diethylaniline, borane-morpholine, borane-4-ethylmorpholine or borane-4-phenylmorpholine complex;

"strong acid" means a protic acid having a pKa of <2, such as $H_2SO_4$, $CH_3SO_3H$ or $CF_3SO_3H$, which acids may optionally be used in the presence of a Lewis Acid, such as $BF_3$;

"acid catalyst" means a suitable acid, such as p-toluenesulfonic acid;

"base" means $Na_2CO_3$, $K_2CO_3$, $NaHCO_3$ or $KHCO_3$;

"strong base" means an alkali metal hydroxide, such as NaOH, KOH or LiOH, an alkaline earth metal hydroxide such as $Ca(OH)_2$, or an alkali metal hydrocarbon, such as n-butyllithium, t-butyllithium or s-butyllithium;

"alkoxide base" means an alkali metal alkoxide, such as $NaOC(CH_3)_3$, $KOC(CH_3)_3$;

"tertiary amine base" means a tertiary amine selected from triethylamine, pyridine and di-isopropylethylamine; and "leaving group" means a halogen selected from Br, Cl or I, or a sulfonate ester of the formula —$OSO_2R^3$, wherein $R^3$ is methyl, trifluoromethyl or 4-methyl-phenyl.

As used herein the following reagents and solvents are identified by the abbreviations indicated: benzotriazol-1-yloxytris[dimethylamino]-phosphonium hexafluoro-phosphate (BOP); para-toluenesulfonic acid (p-TSA); tetrahydrofuran (THF); iso-propanol (i-PrOH); methanol (MeOH); ethyl acetate (EtOAc); tert-butyl methyl ether (t-BuOMe); triethylamine ($Et_3N$); N,N-dimethylformamide (DMF); trifluoroacetic acid (TFA); dimethylsulfoxide (DMSO); borane-tertbutylam ine (TBAB); boron trifluoride etherate ($BF_3.OEt_2$).

Where hydride reducing agents are employed the reduction products formed will be dependent upon the specific hydride reducing agent utilized and the reaction conditions employed. For example, the reduction of ketones can be selectively achieved in presence of other less reactive groups, such as carbamates, by using less reactive hydride reducing agents, such as $NaBH_4$, under appropriate reaction conditions.

The present invention comprises a process for preparing a compound of the formula I as shown in Reaction Scheme 1.

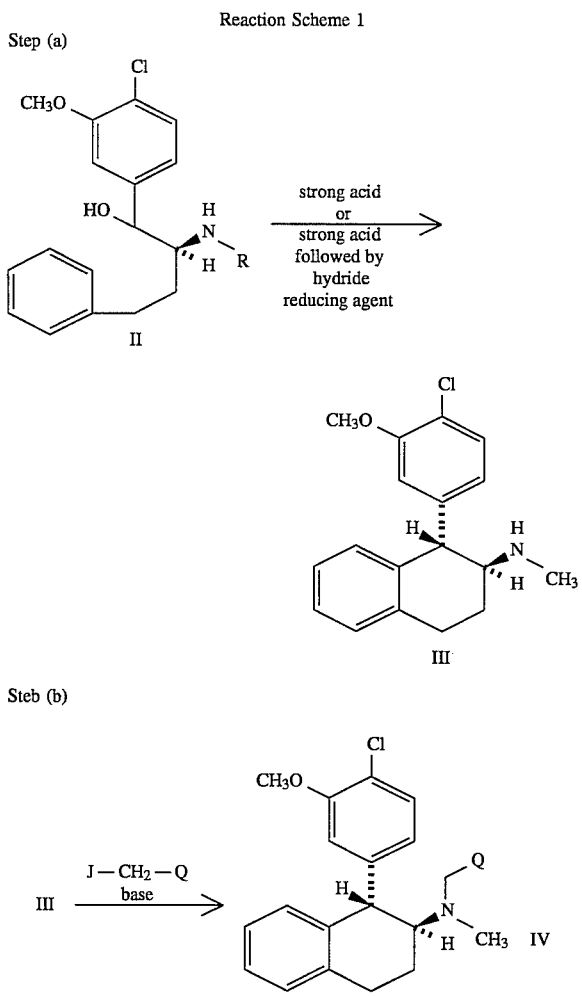

Reaction Scheme 1

-continued
Reaction Scheme 1

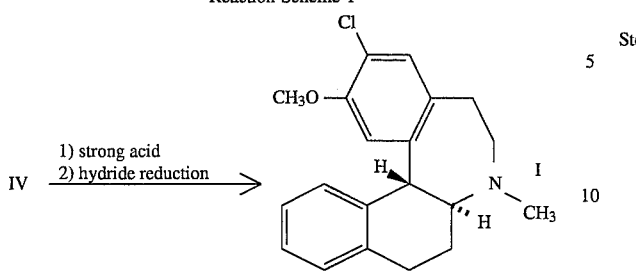

In Scheme 1, Step (a), the alcohol II, wherein R is $CH_3$, is combined with a strong acid, preferably $CF_3SO_3H$, in a suitable solvent, such as $CH_2Cl_2$, at −40° to +20° C., preferably about 0° C., then stirred at 0° to 50° C., preferably about 25° C., for 6 to 24 hours, preferably about 12 hours, to form the amine III.

Alternatively, where R is $-C(O)OR^1$, the alcohol II is treated with a strong acid as described above, then reduced by treating with a hydride reducing agent, preferably $LiAlH_4$, in a suitable solvent, such as THF, at 0° to 80° C., preferably at 65° to 70° C., to form the amine III.

In Step (b), the amine III is reacted with a compound of the formula $J-CH_2-Q$, wherein J and Q are as defined above, preferably J is Br and Q is $-CH(OCH_3)_2$, in the presence of a base, preferably $K_2CO_3$ or $Na_2CO_3$, and a suitable solvent, such as DMF, in a sealed vessel, preferably a Teflon® lined bomb, at a temperature of 60° to 150° C., preferably about 110° C., for 12 h to 120 h, preferably about 24 h to 36 h, to give compound IV.

In Step (c), compound IV is combined with a strong acid, preferably $H_2SO_4$ or $CH_3SO_3H$, in a suitable solvent, such as $CH_2Cl_2$, at −40° to +25° C., preferably 0° to +5° C, then warmed to about 15° to 75° C., preferably 25° to 40° C., for 1 to 18 hours, preferably about 2 to 6 hours. The resulting product is treated with a hydride reducing agent, preferably TBAB or $NaBH_4$, in a suitable solvent, preferably $CH_2Cl_2$ or an alcohol solvent, such as isopropanol, at −30° to 50° C., preferably at 0° to 25° C., for ½ to 5 hours, preferably about 1.5 to 2 hours to give a compound of the formula I.

The present invention further comprises a process as described above wherein the alcohol of Step (a) is prepared according to Process A, as shown in Reaction Scheme A.

Reaction Scheme A

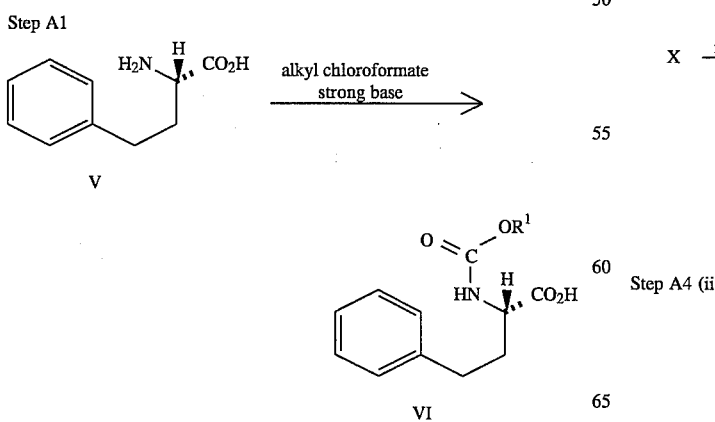

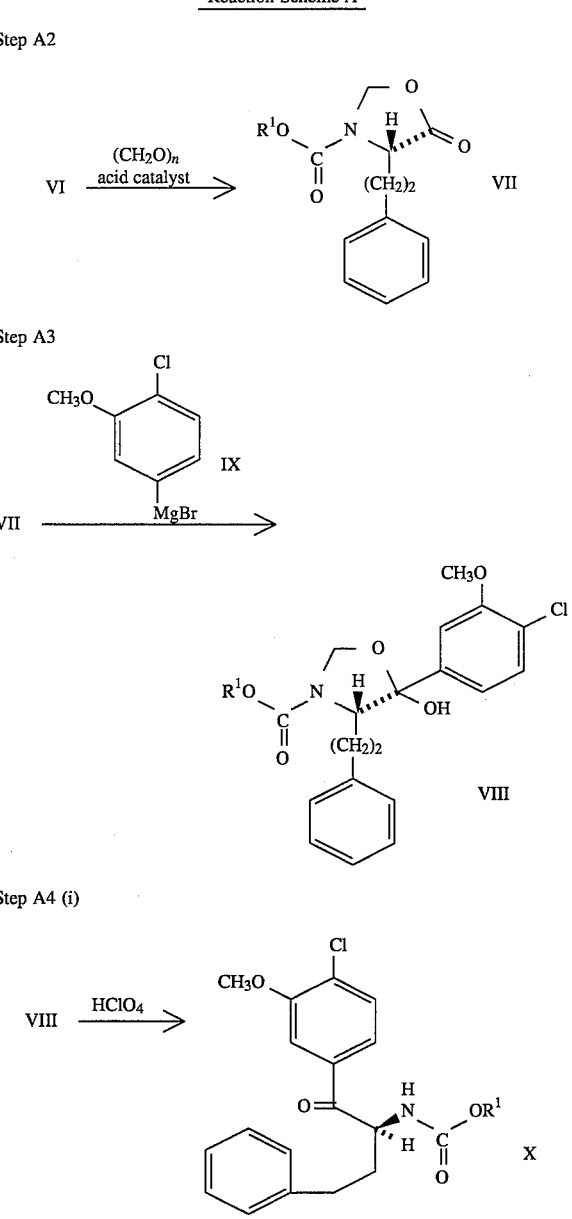

-continued
Reaction Scheme A

VIII —hydride reducing agent→

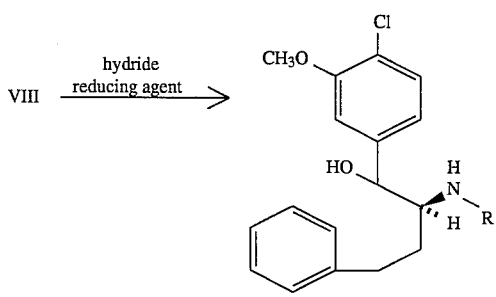

II

In Scheme A, Step A1, L-homophenylalanine (V) is treated with an alkyl chloroformate, preferably ClC(O)OCH₃ or ClC(O)OCH₂CH₃, in the presence of a strong base, such as NaOH, preferably 1N NaOH, and a base, such as Na₂CO₃ or K₂CO₃, at −20° to 20° C., preferably about 0° C., for 30 to 90 min then at 0° C. to 50° C., preferably about 30° C., for 30 to 90 min. Acidify the mixture to pH 1 to 3 by adding acid, preferably HCl, at −10° to 30° C., preferably about 0° C. to form the carbamate VI, wherein $R^1$ is as defined above.

In Step A2, the carbamate VI is treated with paraformaldehyde in the presence of an acid catalyst, preferably pTsOH, and a suitable solvent, such as benzene or toluene, at 40° C. to 120° C., preferably at reflux temperature, to form the oxazolidinone VII, wherein $R^1$ is as defined above.

In Step A3, a Grignard reagent (IX) is prepared from 5-bromo-2-chloroanisole and Mg in a suitable solvent, such as THF, at 0° to 60° C., preferably at 40° to 45° C., then reacted with the oxazolidinone (VII) in a suitable solvent, such as THF, at −50° to +10° C., preferably at −20° to −10° C., for 1 to 6 hours, preferably about 5 hours, then at 0° to 50° C., preferably about 25° C., for 1 to 6 hours, preferably for about 3 hours, to form the oxazolidine VIII, wherein $R^1$ is as defined above.

Alternatively, in Step A3 the oxazolidinone (VII) is reacted with a metal reagent as described for Step B2 of Reaction Scheme B, below, to form the oxazolidine VIII, wherein $R^1$ is as defined above.

In Step A4 (i), the oxazolidine VIII is treated with an acid selected from HCl, BF₃.OEt₂, pTSA or HClO₄, preferably 70% HClO₄, in a suitable solvent, such as THF, at −30° to 20° C., preferably about 0° C., then warmed to 10° to 50° C., preferably about 25° C., for 1 to 6 h, preferably about 3 h, to form the ketone X. The ketone X is treated with a hydride reducing agent, preferably LiAlH₄, in a suitable solvent, such as THF, at −50° to 30° C., preferably about 0° C., then at 40° C. to about 80° C., preferably at reflux temperature, for 2 to 8 h, preferably about 4 h, to form the alcohol II, wherein R is CH₃.

In Step A4 (ii), the oxazolidine VIII is treated with a hydride reducing agent, preferably LiAlH₄, in a suitable solvent, such as THF, at 0° to 50° C., preferably about 25° C., to form the alcohol II, wherein R is CH₃.

Alternatively, in Step A4 (i) or Step A4 (ii), where the hydride reducing agent is preferably LiBH₄ or NaBH₄, the treatment is carried out in a suitable solvent, such as an alcohol, preferably EtOH, at −20° to 20° C., preferably about 0° C., then at 10° to 40° C., preferably about 25° C., to give the alcohol II, wherein R is —C(O)OR¹ and $R^1$ is as defined above.

In an alternative embodiment, the present invention further comprises a process as described above wherein the alcohol of Step (a) is prepared according to Process B, as shown in Reaction Scheme B.

Reaction Scheme B

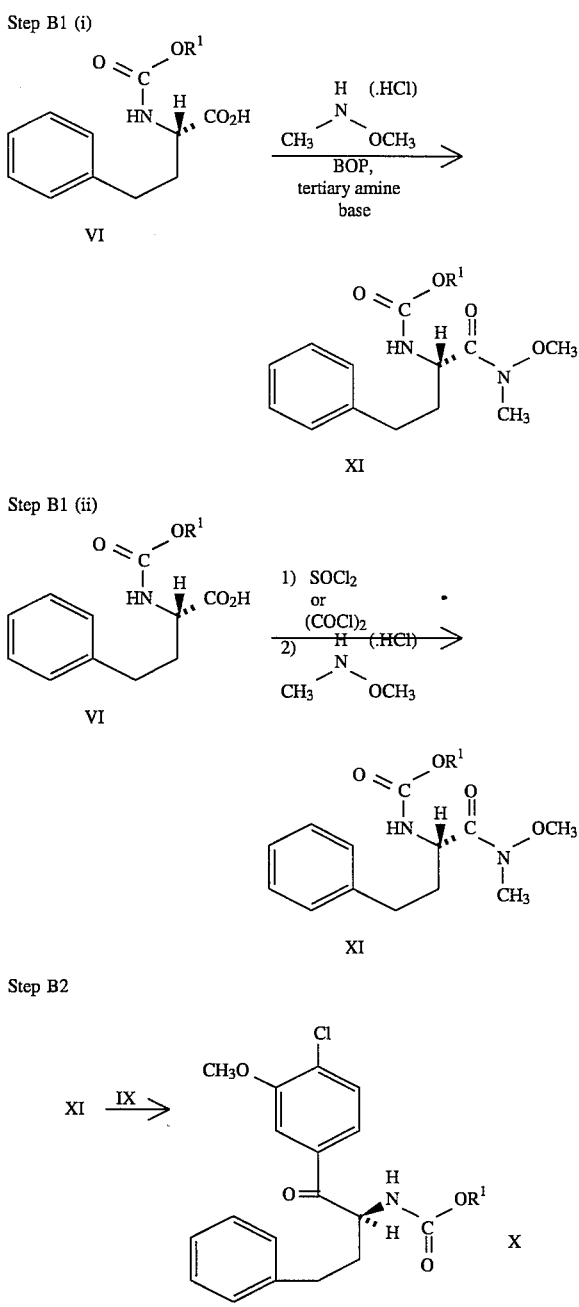

-continued
Reaction Scheme B

Step B3

X —hydride reducing agent→ 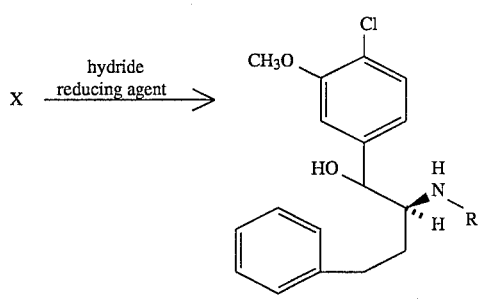 II

Reaction Scheme C

Step C1

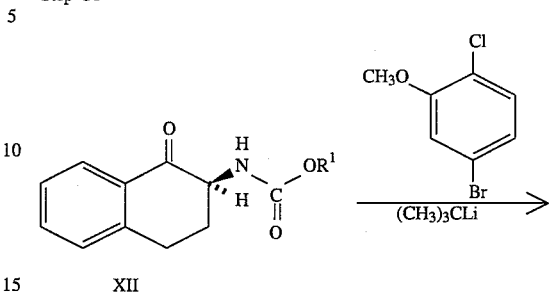

In Scheme B, Step B1 (i), the carbamate VI, from Scheme A, Step A1, is treated with N,O-dimethylhydroxylamine, as the free base or hydrochloride, in the presence of BOP, a tertiary amine base, such as Et$_3$N or pyridine, and a suitable solvent, such as CH$_2$Cl$_2$, at 0° to 50° C., preferably about 25° C., to form compound XI.

Alternatively, in Step B1 (ii), the carbamate VI, from Scheme A, Step A1, is treated with SOCl$_2$ or (COCl)$_2$ to form an acid chloride. The acid chloride is then treated with N,O-dimethylhydroxylamine, as the free base or as the hydrochloride, in the presence of a tertiary amine base, such as pyridine, in a suitable solvent, such as CH$_2$Cl$_2$, at 0° to 50° C., preferably about 25° C., to form compound XI.

In Step B2, compound XI is treated with Grignard reagent IX by the procedure described for Reaction Scheme A, Step A3, to form the ketone X.

Alternatively, in Step B2, compound XI is treated with a metal reagent of the formula

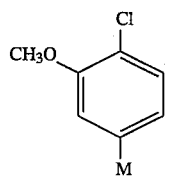

wherein M is selected from ZnL, TiL$_3$, CeL$_2$, MnL or CuL, and L is a halide selected from Br, Cl or I. The reaction is carried out via substantially the same procedure as described for the Grignard reagent in Reaction Scheme A, Step A3, to form the ketone X.

In Step B3, the ketone X is treated with a hydride reducing agent using the procedure described for Scheme A, Step A4(i) or A4(ii), to form the alcohol II.

In a second alternative embodiment, the present invention comprises a process for preparing compound I according to Process C, as shown in Reaction Scheme C.

Step C2

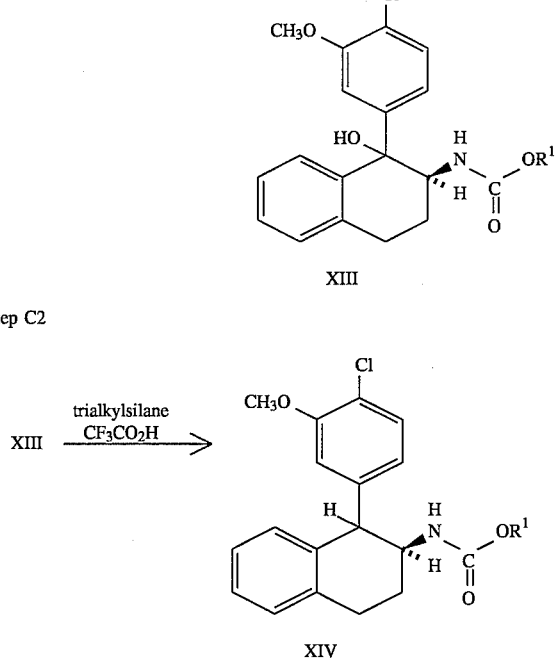

Step C3

Step C4

XIV —hydride reducing agent→ 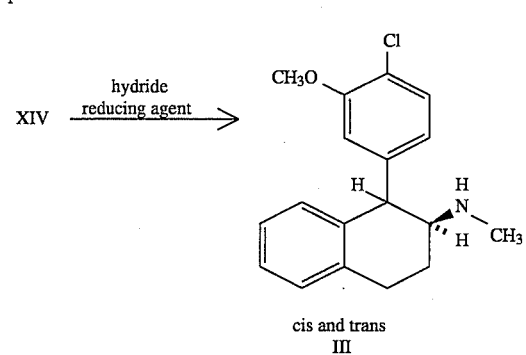

cis and trans
III

Reaction Scheme C
-continued

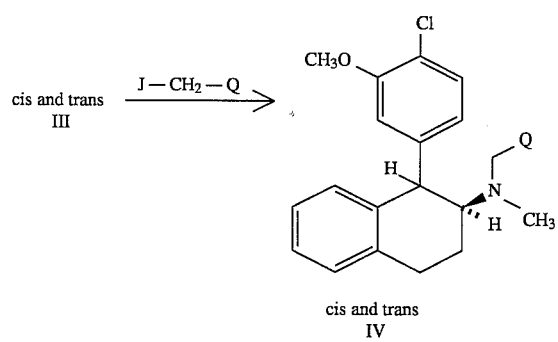

cis and trans III cis and trans IV

Step C5

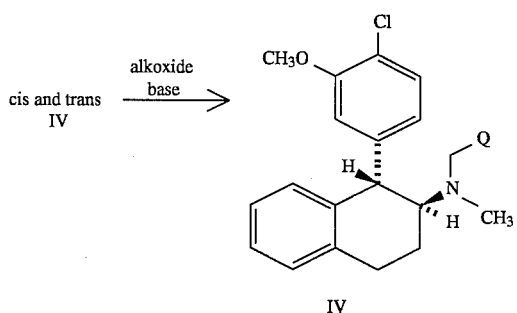

cis and trans IV

IV

Step C6

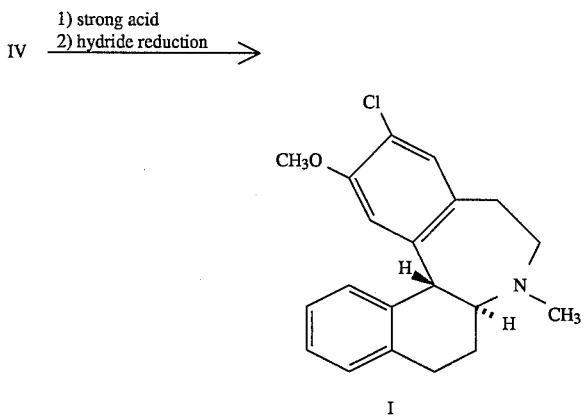

I

In Scheme C, Step C1, 5-bromo-2-chloroanisole is treated with t-butyllithium, preferably a solution of t-butyllithium in pentane, in a suitable solvent, such as $Et_2O$, at −60° to +10° C., preferably about −15° C., for about 1 h. The ketocarbamate XII is added to the resulting mixture and reacted at 0° to 50° C., preferably about 25° C., for 2–8 h, preferably about 4 h, to form compound XIII.

In Step C2, compound XIII is treated with a trialkylsilane, preferably $(CH_3CH_2)_3SiH$, and $CF_3CO_2H$ in a suitable solvent, such as $CH_2Cl_2$, at −20° to 50° C., preferably 0° to 25° C., for 1 to 4 h, preferably about 1 h, to form the product XIV as a mixture of cis and trans isomers.

In Step C3, the cis/trans mixture of compound XIV is treated with a hydride reducing agent, preferably $LiAlH_4$, in a suitable solvent, such as THF, at 30° to 80° C., preferably at reflux temperature, for 30 to 90 min, preferably about 1 h, to give compound III as a mixture of cis and trans isomers.

In Step C4, the cis/trans mixture of compound III is reacted with a compound of the formula $J—CH_2—Q$, wherein J and Q are as defined above, preferably J is Br and Q is $—CH(OCH_3)_2$, by the procedure described for Scheme 1, Step (b), to form the compound IV as a mixture of cis and trans isomers.

In Step C5, the cis/trans mixture of compound IV is treated with an alkoxide base, preferably $KOC(CH_3)_3$ or $NaOC(CH_3)_3$, in the presence of a suitable solvent mixture, such as DMSO/DMF, at −20° to 50° C., preferably 0° to 25° C., to give the compound IV.

In Step C6, compound IV is treated according to the procedure described for Scheme 1, Step (c), to form compound I.

Starting compounds of the formula XII can be prepared via the process shown in Reaction Scheme D.

Reaction Scheme D

Step D1

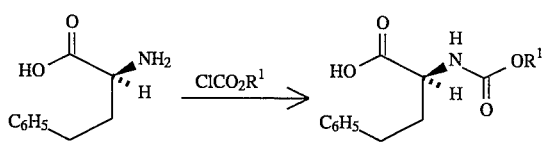

V    XV

Step D2

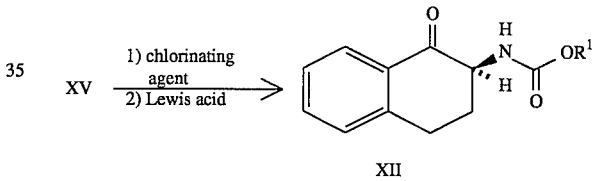

XII

In Reaction Scheme D, Step D1, a combination of the chiral amino acid V, a strong base, preferably NaOH, most preferably 1N aqueous NaOH, and a base, preferably $Na_2CO_3$, at −20° to +20° C., preferably about 0° C, is treated with $ClCO_2R^1$, wherein $R^1$ is as defined above, preferably $R^1$ is $CH_2CH_3$ or $CH_3$, then warmed to 0° to 40° C., preferably about 25° C., for 1 to 5 hours, preferably about 3 hours, then treated with HCl to form the carbamate XV.

In step D2, the carbamate XV is combined with a chlorinating agent, such as $SOCl_2$ or oxalyl chloride, preferably $SOCl_2$, in a suitable solvent, such as $CH_2Cl_2$, and heated at 30° to 70° C., preferably at reflux, for 1 to 10 hours, preferably about 3 hours, then cooled to about 25° C. The resulting mixture is treated with a Lewis acid, preferably $AlCl_3$, in a suitable solvent, such as $CH_2Cl_2$, for 1 to 10 hours, preferably about 3 hours, to give the ketocarbamate XII.

The starting compound of the formula V is commercially available or can be prepared via known methods.

The following preparations and examples illustrate the process of this invention:

PREPARATION 1

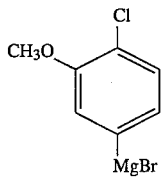

Combine Mg turnings (1.30 g, 54.00 mmol) and 35 mL dry THF. Add a solution of 5-bromo-2-chloroanisole (11.78 g, 53.20 mmol) dissolved in 300 mL dry THF over a 10 min. period, maintaining the reaction temperature at 40°–45° C., and stir for 90 min. The resulting solution of Grignard reagent is used as is.

Grignard concentration is determined by back titration to a phenolphthalein endpoint.

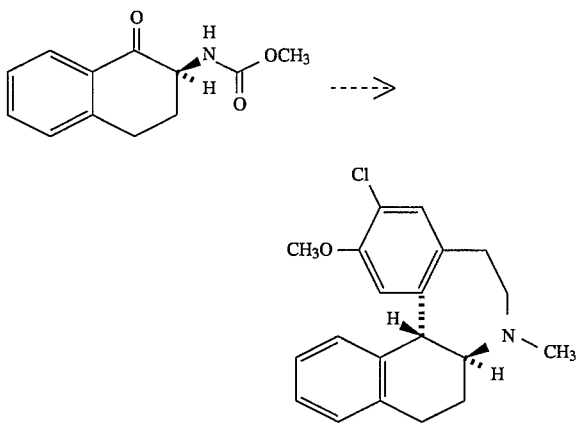

Step (a):

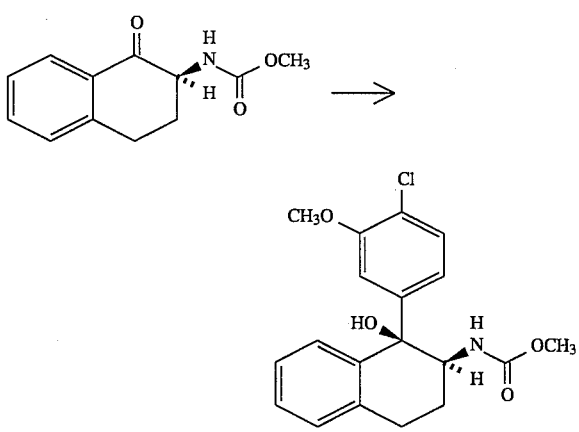

Combine 5-bromo-2-chloroanisole (24.580 g, 110.981 mmol) and 150 mL Et$_2$O, cool to −15° C. then add t-butyllithium (130 mL, 221 mmol, 1.7M in pentane) dropwise over 1 h. Stir for 5 min at −15° C., then add the ketocarbamate (8.0327 g, 36.641 mmol) portionwise over 5 min and stir for 4 h at room temperature. Add 100 mL saturated NH$_4$Cl and 100 mL CH$_2$Cl$_2$, filter, wash the solids with 50 mL CH$_2$Cl$_2$. Add 100 mL saturated NH$_4$Cl to the flitrate and separate the layers. Wash the aqueous layer with 3×50 mL CH$_2$Cl$_2$, wash the combined organic layers with 1×100 mL brine. Dry over anhydrous MgSO$_4$ and concentrate in vacuo to a residue. Flash chromatograph the residue (silica gel, 2:2:1 toluene/hexane/Et$_2$O) to give the product, mp: softens 155°–157° C., melts 167°–168° C. $^1$H NMR (CDCl$_3$) δ: 7.05–7.35 (m, 6H); 6.40 (d, 1H, J=9.4 Hz); 4.40 (d, 1H, J=15 Hz); 4.32 (br. s, 2H); 4.20 (m, 1H); 3.82 (s, 3H); 3.62 (s, 3H); 2.90–3.20 (m, 2H); 1.60–1.90 (m, 2H).

Step (b):

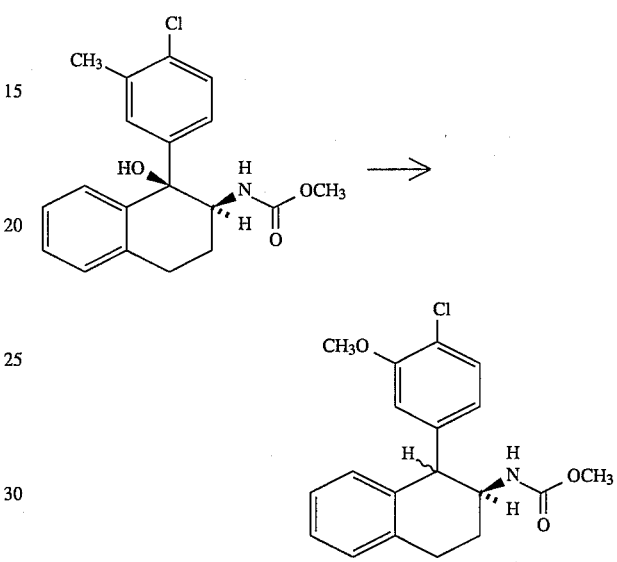

Combine the product of Step (a) (1.137 g, 3.142 mmol) and 10 mL CH$_2$Cl$_2$, cool to 0° C., then add triethylsilane (1.30 mL, 8.14 mmol) and stir for 15 min at room temperature. Cool to 0° C., add TFA (6.10 mL, 79.2 mmol) and stir for 1 h at room temperature. Add 10 mL saturated NaHCO$_3$ and 25 mL CH$_2$Cl$_2$, separate the layers, wash the aqueous layer with 1×25 mL CH$_2$Cl$_2$. Combine the organic layers and wash with 1×20 mL brine, then dry over anhydrous MgSO$_4$ and concentrate in vacuo to yield the product as a mixture of cis and trans isomers. trans isomer: $^1$H NMR (CDCl$_3$) δ: 7.05–7.30 (m, 7H); 6.85 (d, 1H, J=7.5 Hz); 6.71 (s, 1H); 6.55 (dd, 1H, J=1.5, 7.5 Hz); 4.80 (br. s, 1H); 4.08 (br. s, 2H); 3.82 (s, 3H); 3.61 (s, 3H); 2.85–3.07 (m, 2H); 2.05–2.15 (m, 1H); 1.70–1.90 (m, 1H). cis isomer: $^1$H NMR (CDCl$_3$) δ: 6.47–7.25 (m, 7H); 4.20–4.50 (m, 3H); 3.80 (s, 3H); 3.67 (s, 3H); 3.02 (m, 2H); 1.68–1.90 (m, 2H).

Step (c):

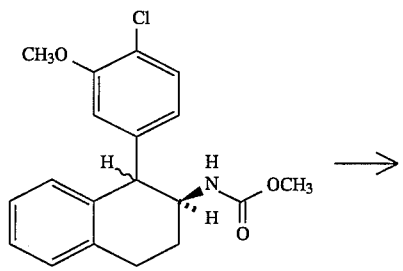

-continued

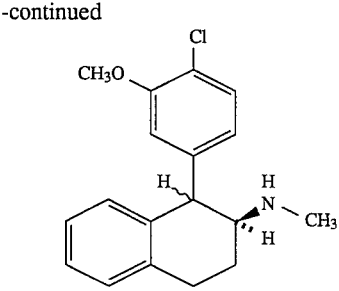

Dissolve the cis/trans product of Step (b) (364.4 mg, 0.881 mmol) in 5 mL THF, add LiAlH₄ (2.80 mL, 2.80 mmol, 1M in Et₂O) and heat at reflux for 1 h. Cool to room temperature then add 10 mL saturated NaHCO₃ and 25 mL CH₂Cl₂. Separate the layers and wash the aqueous layer with 2×10 mL CH₂Cl₂. Combine the organic layers, wash with 1×10 mL saturated salt, dry over anhydrous MgSO₄ and concentrate *in vacuo* to yield the product as a mixture of cis and trans isomers. trans isomer: ¹H NMR (CDCl₃) δ: 6.17–7.32 (m, 7H); 3.90 (d, 1H, J=7.5 Hz); 3.85 (s, 3H); 2.80–3.0 (m, 3H); 2.40 (s, 3H); 2.20–2.30 (m, 1H); 1.30–1.80 (m, 2H). cis isomer: ¹H NMR (CDCl₃) δ: 6.52–7.35 (m, 7H); 4.35 (d, 1H, J=5.6 Hz); 3.81 (d, 1H, J=7.5 Hz); 2.85–3.10 (m, 3H); 2.50 (s, 3H); 1.30–1.99 (m, 3H).

Step (d):

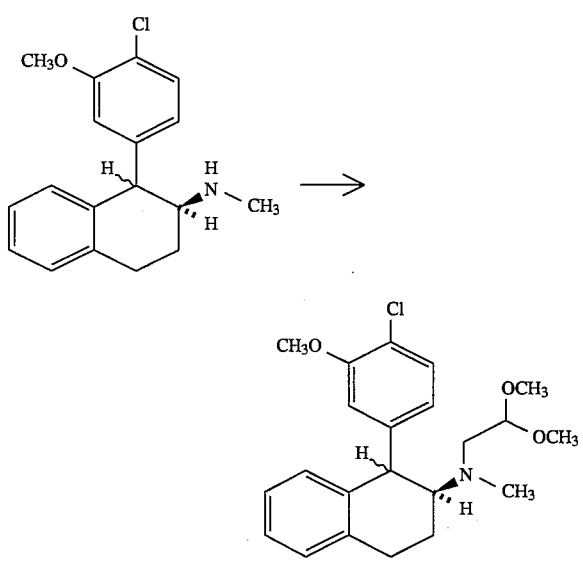

Combine the cis/trans product of Step (c) (2.01 g, 6.66 mmol), K₂CO₃ (9.282 g, 66.7 mmol, milled), bromoacetaldehyde dimethyl acetal (4.00 mL, 33.8 mmol) and 20 mL DMF in a Teflon® acid digestion bomb, seal and heat at about 110° C. for 3 days. Cool to room temperature, add 25 mL saturated NaHCO₃, 25 mL water and 50 mL t-BuOMe, and separate the layers. Wash the aqueous layer with 2×50 mL t-BuOMe, then wash the combined organic layers with 3×25 mL water and 1×10 mL brine. Dry over MgSO₄ and concentrate in vacuo to a residue. Flash chromatograph the residue (silica gel, 30–50% EtOAc/hexanes) to yield the product as a mixture of trans and cis isomers (1:3.6 ratio). trans isomer: ¹H NMR (CDCl₃) δ: 6.65–7.30 (m, 7H); 4.12 (t, 1H, J=5.6 Hz); 4.09 (d, 1H, J=1 1.3 Hz); 3.82 (s, 3H); 3.21 (s, 3H); 3.12 (s, 3H); 2.95 (m, 3H); 2.60 (dd, 2H, J=5.6, 11.3 Hz); 2.31 (s, 3H); 2.08 (m, 1H); 1.70–1.80 (m, 1H). cis isomer: ¹H NMR (CDCl₃) δ: 6.65–7.35 (m, 7H); 4.51 (t, 1 H, J=5.6 Hz); 4.09 (d, 1H, J=1 1.3 Hz); 3.82 (s, 3H); 3.40 (2s, 6H); 2.40–2.90 (m, 3H); 2.32 (s, 3H); 2.25 (m, 1H); 2.08 (m, 1H); 1..51–1.81 (m, 1H).

Step (e):

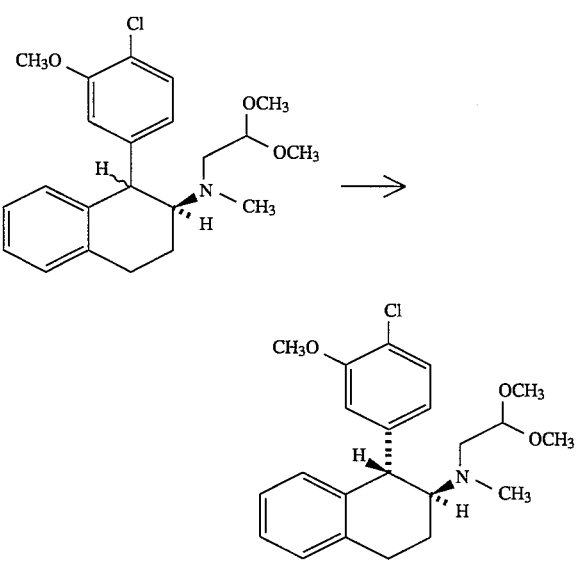

Dissolve the cis/trans product of Step (d) (280.9 mg, 0.720 mmol) in 2 mL of freshly degassed DMSO. Add 1 mL freshly degassed DMF, cool to 0° C., add KOC(CH₃)₃ (172.8 mg, 1.540 mmol) and stir for 1 h at room temperature. Add 15 mL saturated NaHCO₃, 20 mL t-BuOMe and 5 mL water. Separate the layers and wash the aqueous layer with 3×15 mL t-BuOMe. Combine the organic layers, wash with 4×5 mL water, dry over anhydrous MgSO₄ and concentrate in vacuo to yield a 51:1 mixture of the trans and cis isomers. Flash chromatograph (silica gel, 30–50% EtOAc/hexanes) to give the trans product. ¹H NMR (CDCl₃) δ: 6.65–7.30 (m, 7H); 4.12 (t, 1H, J=5.6 Hz); 4.09 (d, 1H, J=1 1.3 Hz); 3.82 (s, 3H); 3.21 (s, 3H); 3.12 (s, 3H); 2.95 (m, 3H); 2.6 (dd, 2H, J=5.6, 11.3 Hz); 2.31 (s, 3H); 2.08 (m, 1H); 1.70–1.80 (m, 1H). Step (f):

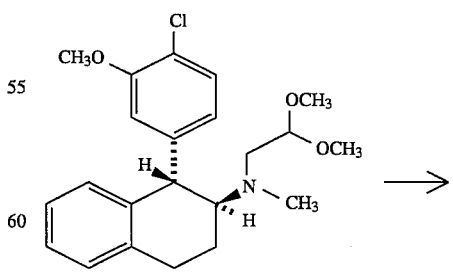

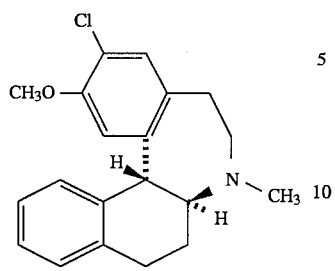

Combine methanesulfonic acid (7.40 g, 77.003 mmol) and 15 mL CH$_2$Cl$_2$ and cool to 0° to 5° C. Dissolve the product of Step (e) (2.34 g, 6.001 mmol) in 15 mL CH$_2$Cl$_2$ and add the resulting solution to the acid solution over a 5 min period. Heat the mixture at 40° C. for 2 h, then concentrate (50° C./20 Torr) to a residue. Dissolve the residue in 10 mL CH$_2$Cl$_2$, cool to 10° to 15° C., and add a solution of NaBH$_4$ (0.280 g, 7.402 mmol) in 15 mL i-PrOH over a 10 min period. Stir for 2 h, then add a solution of Na$_2$CO$_3$ (6.70 g, 63.208 mmol) in 34 mL water to adjust to pH 7. Extract the aqueous layer with 2×10 mL CH$_2$Cl$_2$, wash the combined organic layers with 2×10 mL water, then dry over anhydrous MgSO$_4$ and concentrate in vacuo to yield the (−)-enantiomer of the title compound. Purify by flash chromatograph (silica gel, 2.5–10% MeOH/CH$_2$Cl$_2$). $^1$H NMR (CDCl$_3$) δ: 6.95–7.19 (m, 5H); 5.88 (s, 1H); 4.78 (d, 1H, J=7.5 Hz); 3.5–3.62 (m, 1H); 3.49 (s, 3H); 3.2 (dd, 1H, J=3.75, 11.3 Hz); 2.65–2.86 (m, 4H); 2.51 (s, 3H); 2.41 (dd, 1H, J=5.6, 11.3 Hz); 1.98–2.18 (m, 1H); 1.6–1.8 (dq, 1H, J=5.6, 11.3 Hz).

Using substantially the same procedure, the title compound can be prepared from the product of Step (e) using H$_2$SO$_4$ in place of methanesulfonic acid.

EXAMPLE 2

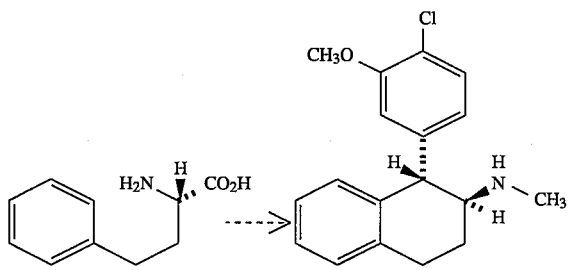

Step (a):

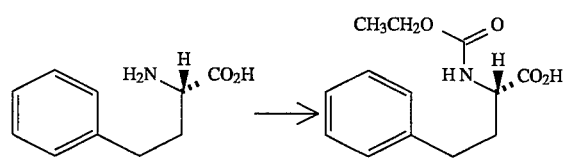

Combine L-homophenylalanine (25.0 g, 0.139 mole) and 1.0N NaOH (280 mL, 0.280 mole), add 1.5 eq of Na$_2$CO$_3$ (22.2 g, 0.209 mole) and cool to 0 ° C. Add ethyl chloroformate (30.4 g, 0.280 mole) dropwise, stir for 1.0 h then warm to 30 ° C. and stir for an additional hour. Cool to 0 ° C. and acidify to pH=2 with 10% aq HCl. Add 200 mL of CH$_2$Cl$_2$, separate the layers and wash the aqueous layer with 2×200 mL of CH$_2$Cl$_2$. Combine the organic layers, wash with brine, then dry over MgSO$_4$. Concentrate/n vacuo to give the carbamate product. $^1$H NMR (CDCl$_3$) δ: 7.4–7.2 (SH, m); 5.22 (1H, d, J=7.1Hz); 5.5–5.4 (1H, m); 4.19 (2H, q, J=6.9 Hz), 2.77 (2H, t, J-7.9 Hz); 2.4–2.2 (1H, m); 2.1–2.0 (1H, m); 1.30 (3H, t, J=7.0 Hz).

Step (b):

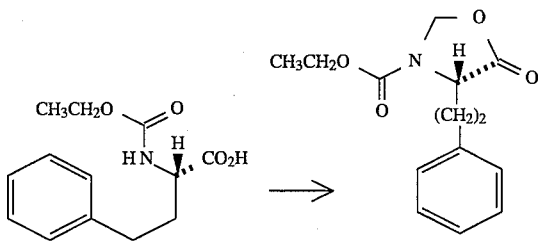

Combine the carbamate of Step (a) (20.0 g, 79.6 mmol), paraformaldehyde (4.80 g, 160 mmol), p-TSA (0.908 g, 4.77 mmol) and 800 mL of benzene. Heat the mixture at reflux using a Dean-Stark trap to remove water until TLC (silica gel, 30% EtOAc/hexane) shows no unreacted starting material. Dilute the reaction mixture with 100 mL of EtOAc, then wash with 10 mL of 0.3M Na$_2$CO$_3$ and 2×25 mL of brine. Dry over MgSO4 and evaporate to give the oxazolidinone product. $^1$H NMR (CDCl$_3$) δ7.4-7.2 (5H, m); 5.55 (1 H, s); 5.22 (1H, d, J=3 Hz); 4.4- 4.1 (3H, m); 2.9-2.7 (2H, m); 2.4-2.2 (2H, m); 1.32 (3H, t, J=5 Hz).

Step (c):

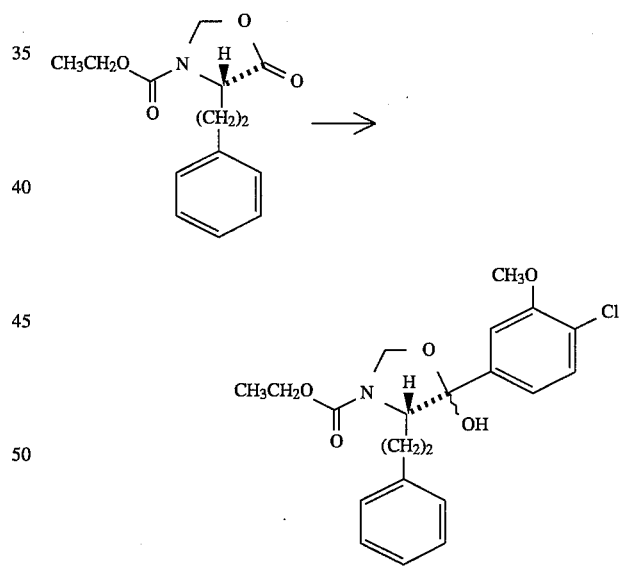

Stir a solution of oxazolidinone of Step (b) (5.00 g, 19.1 mmol) in 19.1 mL of dry THF at −15° C. under nitrogen and add 1.12 eq of the Grignard reagent from Preparation 1 via syringe pump at a rate of 0.57 mL/min. Allow the mixture to warm to room temperature and stir for 3 h. Cool to 0 ° C., then quench with 20 mL of 5% HCl. Add 250 mL EtOAc, separate the layers and wash the aqueous layer with 50 mL of EtOAc. Combine the organic layers and wash with brine, then dry over MgSO$_4$ and concentrate in vacuo to a residue. Purify the residue by flash chromatography (silica gel, 97:3 to 92:8 EtOAc/CH$_2$Cl$_2$) to give oxazolidine product as a mixture of diastereomers. $^1$H NMR (CDCl$_3$) δ: 7.5-7.0 (8H, m); 5.8-5.7 (m); 5.5-5.3 (m); 5.1-4.8 (m); 4.3-4.1 (m); 3.88 (3H, s); 3.9-3.3 (m); 2.9-2.6 (m); 2.3-2.1 (m); 1.68 (3H, s); 1.4-1.1 (m).

Step (d):

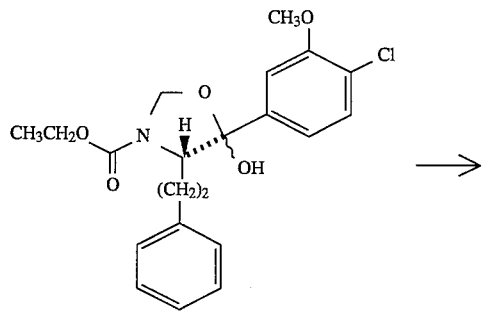

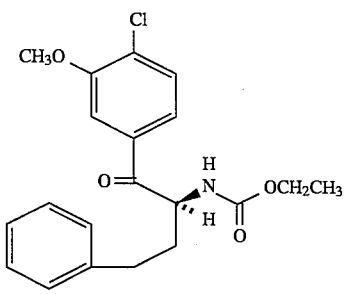

Combine the oxazolidine product of Step (c) (1.86 g, 4.6 mmol), water (3.9 g, 21.5 mmol) and 18 mL of THF, and cool to 0° C. Add 70% HClO$_4$ (6.12 g, 15.4 mmol) dropwise over 10 min, then warm to room temperature and stir for 3 h. Quench the reaction with 30 mL of aq NaHCO3 and extract with EtOAc (3×30 mL). Combine the organic layers and wash with brine. Dry over MgSO$_4$ and concentrate in vacuo to a residue. Purify the residue by flash chromatography (99:1 to 97:3 EtOAc/CH$_2$Cl$_2$) to give the ketone product. $^1$H NMR (CDCl$_3$) δ: 7.5-7.2 (8H, m); 5.66 (1H, d, J=8.1 Hz); 5.35 (1 H, dt, J=3.6, 8.3 Hz); 4.21 (2H, q, J=7.1 Hz); 3.91 (3H, s); 2.8-2.6 (2H, m); 2.3-2.1 (1 H, m); 2.0-1.8 (1H, m); 1.32 (3H, t, J=7.1 Hz).

Step (e):

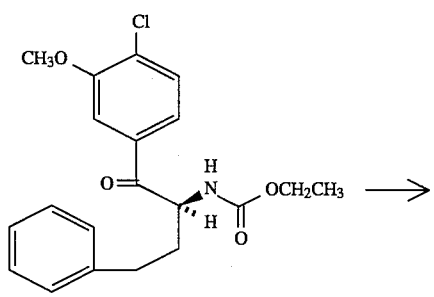

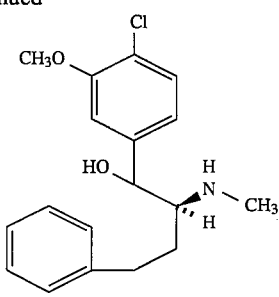

Add LiAlH$_4$ (1M in ether, 4.5 mL, 4.5 mmol) to a mixture of the ketone of Step (d) (0.34 g, 0.90 mmol) and 9 mL of THF at 0° C. Heat the mixture at gentle reflux for 4 h. Cool to room temperature and quench with aqueous saturated NH$_4$Cl. Extract the crude product with Et$_2$O, wash the organic layer with brine, dry over MgSO$_4$ and concentrate in vacuo to give the alcohol product. $^1$H NMR (CDCl$_3$) δ: 7.4-6.8 (8H, m); 4.95 (1 H, d, J=3 Hz), 4.42 (1 H, d, J=5 Hz); 3.93 (3H, s); 2.7-2.4 (3H, m); 2.58 (3H, s); 2.07 (1H, s), 1.8-1.5 (2H, m).

Step (f):

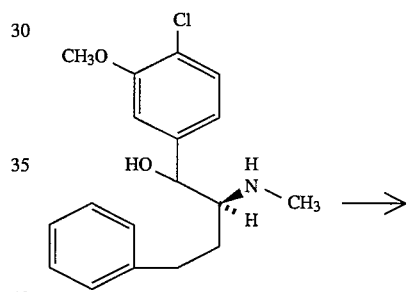

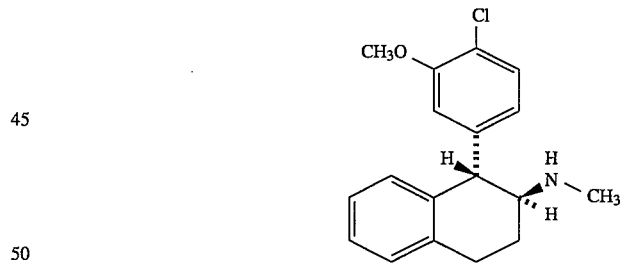

Add CF$_3$SO$_3$H (131 mg, 0.87 mmol) to a mixture of the alcohol of Step (e) (0.014 g, 0.044 mmol) and 0.1 mL CH$_2$Cl$_2$ at 0° C. Warm to room temperature and stir overnight. Dilute the mixture with Et$_2$O and basify with saturated NaHCO$_3$. Separate the organic layer, wash with brine, dry over MgSO$_4$ and concentrate in vacuo to give the title compound. $^1$H NMR (CDCl$_3$) δ: 7.4-7.1 (4H, m); 6.8-6.7 (3H, m); 3.96 (1H, d, J=6 Hz); 3.90 (3H, s); 3.03 (2H, t, J=5 Hz); 2.92 (1 H, dt, J=2 6 Hz); 2.48 (3H, s); 2.3-2.2 (1H, m); 1.8-1.6 (1H, m).

EXAMPLE 3

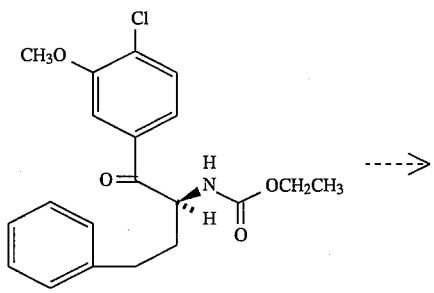

Step (a):

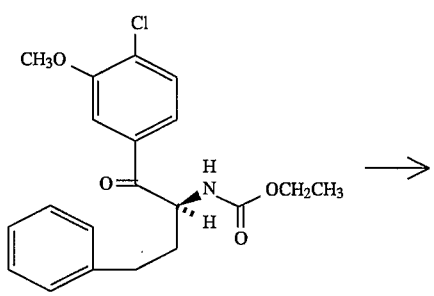

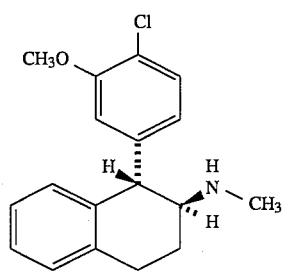

Add NaBH₄ (0.055 g, 1.3 mmol) to a solution of the ketone of Example 2, Step (d) (0.50 g, 1.3 mmol) in 13 mL of EtOH at 0° C., then allow the mixture to warm to room temperature. Monitor the reaction by TLC (silica gel, 7:3 hexane/EtOAc). When the reaction is complete, quench with 8 mL of saturated NaHCO₃, filter and wash the solids with Et₂O. Concentrate the flitrate in vacuo to a residue, dissolve the residue in Et₂O, wash sequentially with saturated NaHCO₃, and brine, then dry over MgSO₄. Concentrate in vacuo to give the alcohol product. ¹H NMR (CDCl₃) δ: 7.4-6.8 (7H, m); 4.9-4.7 (2H, m); 4.22 (2H, q, J=9 Hz); 3.92 (3H, s); 4-3.9 (1H, m); 3.05 (1H, s); 2.8-2.7 (1H, m); 1.7-1.5 (1H, s); 1.9-1.5 (2H, m); 2.32 (3H, t, J=9 Hz).

Step (b):

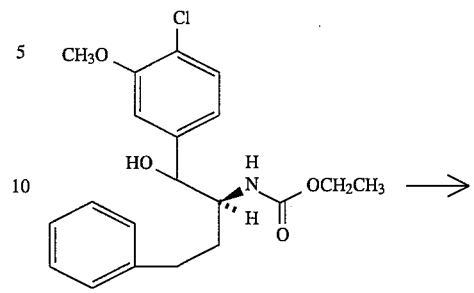

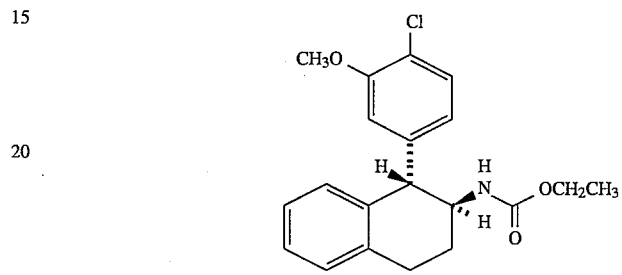

Add CH₃SO₃H (0.41 g, 0.43 mmol) to a solution of the alcohol product of Step (a) (0.160 g, 0.423 mmol) in 2.0 mL CH₂Cl₂ at 0° C., then warm to room temperature and stir overnight. Dilute the reaction mixture with 20 mL of Et₂O, basify with 5.0 mL of saturated NaHCO₃ and separate the organic layer. Wash the aqueous layer with 2×20 mL of Et₂, combine the organic layers, wash with 5.0 mL of brine, and dry over MgSO₄. Concentrate in vacuo to residue and purify the residue by preparative TLC (silica gel, 30:70 EtOAc/hexane) to give the product. ¹H NMR (CDCl₃) δ: 7.4-7.1 (4H, m); 6.92 (1 H, d, J=7.4 Hz); 6.79 (1H, s); 6.62 (1H, dd, J=1.8, 8.1 Hz); 4.87 (1H, s); 4.2-4.1 (4 H, m); 3.90 (3H, s); 3.1-2.9 (2H, m); 2.2-2.1 (1H, m); 1.9-1.8 (1H, m); 1.26 (3H, t, J=7.0 Hz).

Step (c):

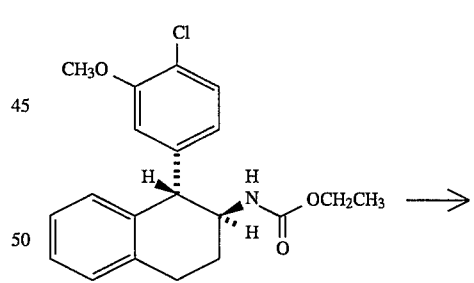

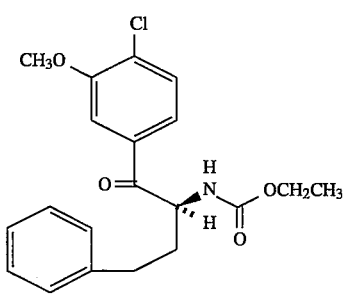

Add 1M solution of LiAlH₄ in Et₂O (1.34 mL, 1.34 mmol) to a solution of the Product of Step (b) (0.120 g, 0.334 mmol) in 3.3 mL of dry THF. Heat the mixture at reflux and monitor the reaction by TLC. When the reaction is complete, cool the mixture to room temperature, and quench with saturated NH₄Cl. Extract with Et₂O (3×20 mL), combine the organic layers, wash with brine and dry over MgSO₄. Concentrate in vacuo and purify the resulting residue by preparative TLC (silica gel, 100:10:1 CH₂Cl₂/MeOH/NH₄OH) to give the title compound.

EXAMPLE 4

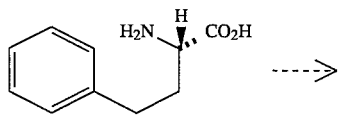

Step (a):

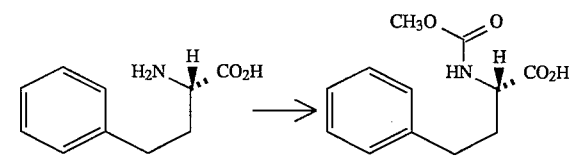

React L-homophenylalanine with methyl chloroformate according to the procedure described for Example 2, Step (a) to form the carbamate product. ¹H NMR (CDCl₃) δ: 7.4-7.2 (5H, m); 5.4-5.3 (1 H, m); 4.5 (1H, m); 3.77 (3H, s); 2.78 (2H, t, J=8.0 Hz); 2.3 (1H, m); 2.1 ( 1H, m).
Step (b):

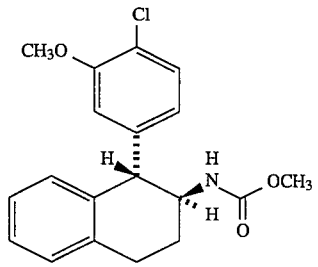

Add Et₃N (1.26 g, 12.5 mmol) to a solution of the product of Step (a) (2.97 g, 12.5 mmol) in 60 mL CH₂Cl₂. Add a solution of BOP (5.53 g, 12.5 mmol) in 30 mL CH₂Cl₂ and stir for 20 min at room temperature. Add N,O-dimethylhydroxylamine hydrochloride (1.34 g, 13.7 mmol) and Et₃N (1.26 g, 12.5 mmol), and stir the mixture while monitoring by TLC (silica gel, 95:5 CH₂Cl₂/MeOH), adding Et₃N (1.26 g, 12.5 mmol) to ensure completion of the reaction. Add 300 mL of CH₂Cl₂ and wash sequentially with 2×125 mL of 10% HCl, saturated aq NaHCO₃ and brine. Dry the organic layer over MgSO₄ and concentrate in vacuo to a residue. Purify the residue by flash chromatography (silica gel, 98.5:1.5 CH₂Cl₂/MeOH) to give the product. ¹H NMR (CDCl₃) δ: 7.3-7.2 (5H, m); 5.53 (1H, d, J=9.0 Hz); 4.8-4.7 ( 1H, m); 3.75 (3H, s); 3.67 (3H, s); 3.22 (3H, s); 2.9-2.6 (2H, m); 2.2-1.9 (2H, m).
Step (c):

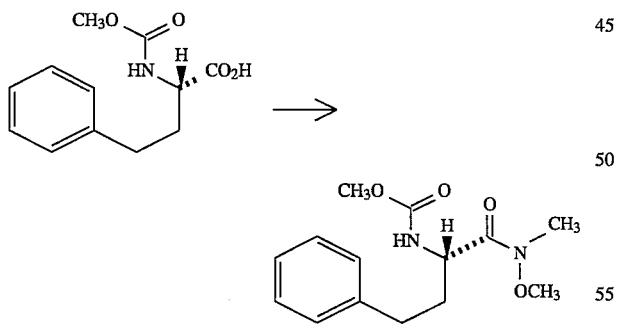

Add 2.5 eq of the Grignard reagent from Preparation 1, dropwise, to a solution of the product of Step (b) (0.477 g, 1.70 mmol) in 6 mL of dry THF at 0° C. Stir the mixture and warm to room temperature, while monitoring by TLC (silica gel, 95:5 hexane/EtOAc), until the reaction is complete. Quench the reaction with 10 mL of EtOH and 10 mL of 5% HCl, and extract with a solution of 1:1 CH₂Cl₂/Et₂O. Dry the organic layer over MgSO₄, concentrate in vacuo and purify the resulting residue by flash chromatography (silica gel, 95:5→85:15, EtOAc/hexane) to give the ketone product. ¹H NMR (CDCl₃) δ: 7.4-7.2 (8H, m); 5.72 (1H, d, J=8 Hz); 5.33 (1H, dt, J=4, 8 Hz); 3.89 (3H, s); 2.8-2.6 (2H, m); 2.3-2.1 (1H, m); 2.0-1.8 (1H, m).

Step (d):

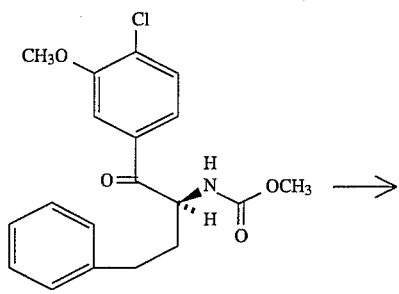

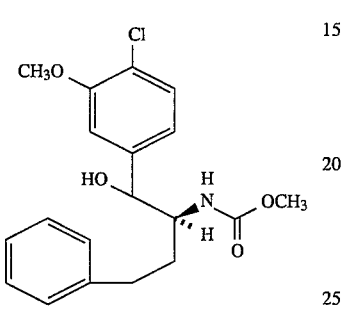

The product of Step (c) is reacted with NaBH₄ according to the procedure described for Example 3, Step (a), to give the alcohol product. $^1$H NMR (CDCl₃) δ: 7.4-7.0 (5H, m); 6.9-6.8 (2H, m); 4.9-4.8 (2H, m); 4.0-3.9 (1H, m); 3.90 (3H, s); 3.75 (3H, s); 2.95 (1H, s); 2.8- 2.5 (2H, m); 1.9-1.5 (2H, m).

Step (e):

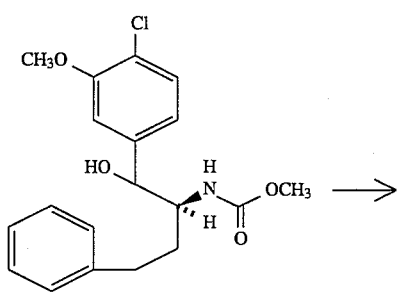

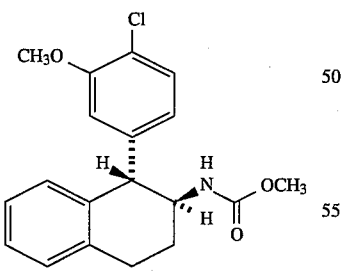

The product of Step (d) is reacted with CH₃SO₃H according to the procedure of Example 3, Step (b), to give the title compound. $^1$H NMR (CDCl₃) δ: 7.3-7.1 (4H, m); 6.93 (1H, d, J=7.8 Hz); 6.8 (1H, s); 6.64 (1H, dd, J=1.8, 9.8 Hz); 4.92 (1H, s); 3.91 (3H, s); 3.70 (3H, s); 3.2-2.9 (2H, m); 2.2-2.1 (1H, m); 2.0-1.8 (1H, m).

We claim:

1. A process for preparing a compound of the formula

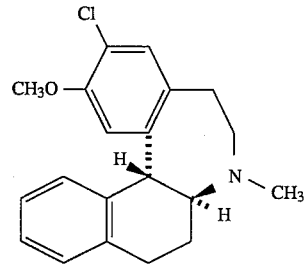

comprising the steps:

(a) cyclizing an alcohol of the formula

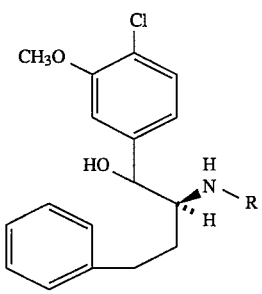

wherein R is —CH₃ or —C(O)—OR¹, and R¹ is C₁-C₆ alkyl or —CH₂C₆H₅, by treating with a strong acid; and, where R is —C(O)—OR¹, reducing the cyclized product with a hydride reducing agent; to form an amine of the formula

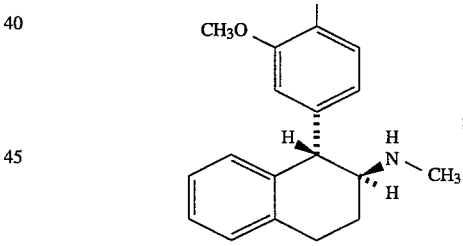

(b) reacting the amine of Step (a) with a compound of the formula J—CH₂—Q, wherein J is a leaving group, and Q is a group of the formula

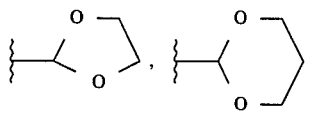

or —CH(OR²)₂, wherein R² is C₁-C₆ alkyl, in the presence of a base to form a compound of the formula

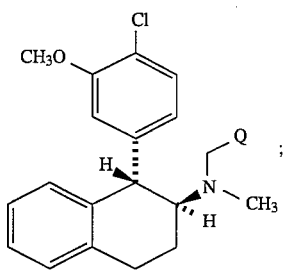

(c) cyclizing the product of step (b) by treating with a strong acid, and treating the cyclized product with a hydride reducing agent.

2. A process of claim 1 wherein the alcohol of step (a) is prepared by a process comprising the steps:

(A1) treating L-homophenylalanine with an $C_1$-$C_6$ alkyl or benzyl chloroformate in the presence of a strong base to form a carbamate of the formula

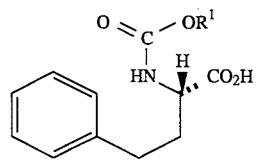

wherein $R^1$ is as defined above;

(A2) treating the carbamate of step (A1) with paraformaldehyde in the presence of an acid catalyst to form an oxazolidinone of the formula

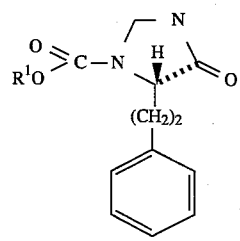

wherein $R^1$ is as defined above;

(A3) treating the oxazolidinone of step (A2) with a reagent of the formula

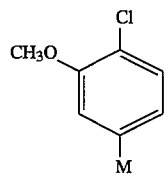

wherein M is selected from MgL, ZnL, $TiL_3$, $CeL_2$, MnL or CuL, and L is a halide selected from Br, Cl or I, to form a 5-hydroxy-oxazolidine of the formula

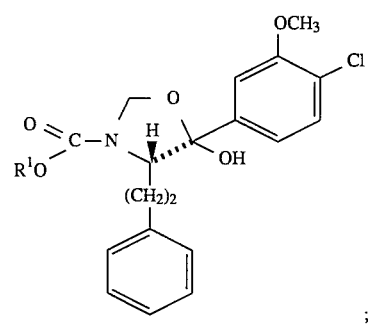

(A4) converting the 5-hydroxyoxazolidine of step (A3) to an alcohol of Step (a) by:

(i) treating the 5-hydroxyoxazolidine with an acid selected from $BF_3.OEt_2$, HCl, p-TSA and $HClO_4$ to form a ketone of the formula

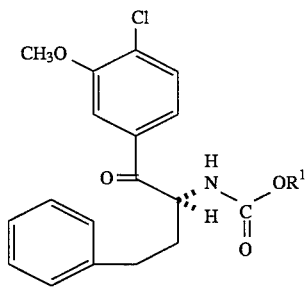

wherein $R^1$ is as defined above, and treating the ketone of step (A4) with a hydride reducing agent; or (ii) treating the 5-hydroxyoxazolidine with a hydride reducing agent; to form the alcohol of Step (a).

3. A process of claim 1 wherein the alcohol of step (a) is prepared by a process comprising the steps:

(B1) treating the carbamate of step (A1) of Process A:

(i) with $CH_3O$—$N(H)CH_3$ or $CH_3O$—$N(H)CH_3$. HCl in the presence of BOP and a tertiary amine base; or (ii) with $SOCl_2$ or $(COCl)_2$ to form an acid chloride and treating the acid chloride with $CH_3O$—$N(H)CH_3$ or $CH_3O$—$N(H)CH_3$.HCl and pyridine; to give a compound of the formula

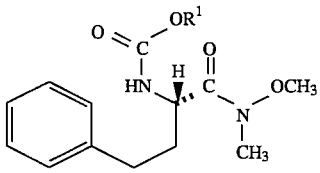

wherein $R^1$ is as defined above;

(B2) treating the product of step (B1) with a reagent of the formula

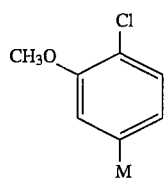

wherein M is selected from MgL, ZnL, TiL$_3$, CeL$_2$, MnL or CuL, and L is a halide selected from Br, Cl or I, to form a ketone of the formula

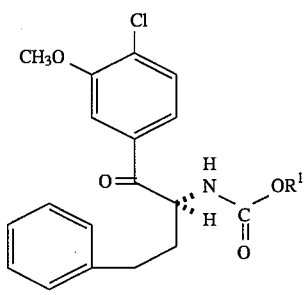

wherein R$^1$ is as defined above;

(B3) treating the ketone of step (B2) with a hydride reducing agent to form the alcohol of Step (a).

4. A process according to claim 1 wherein the hydride reducing agent of Step (a) is LiAlH$_4$; J is Br; and Q is —CH(OR$^2$)$_2$ and R$^2$ is CH$_3$.

5. A process according to claim 4 wherein: the strong acid of Step (a) is CH$_3$SO$_3$H; the strong acid of Step (c) is H$_2$SO$_4$ or CH$_3$SO$_3$H; and the hydride reducing agent of Step (c) is TBAB or NaBH$_4$.

6. A process according to claim 2 wherein: R$^1$ is CH$_3$— or CH$_3$CH$_2$—; the alkyl chloroformate of Step (A1) is methyl or ethyl chloroformate; the strong base of Step (A1) is NaOH or KOH; the acid catalyst of Step (A2) is p-toluenesulfonic acid; M is MgBr; and the hydride reducing agents of Steps (A4) (i) and (A4) (ii) are independently selected from LiBH$_4$, LiAlH$_4$ or NaBH$_4$.

7. A process according to claim 3 wherein: R$^1$ is CH$_3$— or CH$_3$CH$_2$—; the tertiary amine base of Step (B1) is pyridine or triethylamine; M is MgBr; and the hydride reducing agent of Step (B3) is LiBH$_4$, LiAlH$_4$ or NaBH$_4$.

8. A compound of the formula

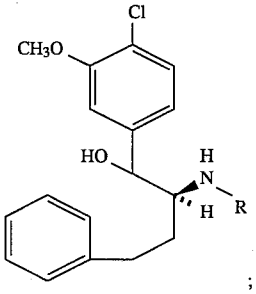

wherein R is —CH$_3$ or —C(O)—OR$^1$, and R$^1$ is C$_1$-C$_6$ alkyl or —CH$_2$C$_6$H$_5$.

* * * * *